(12) United States Patent
Lawless

(10) Patent No.: US 8,735,851 B2
(45) Date of Patent: May 27, 2014

(54) DEVICE AND METHOD FOR QUANTIFYING A SURFACE'S CLEANLINESS

(76) Inventor: John L. Lawless, Pacifica, CA (US)

( * ) Notice: Subject to any disclaimer, the term of this patent is extended or adjusted under 35 U.S.C. 154(b) by 145 days.

(21) Appl. No.: 13/532,022

(22) Filed: Jun. 25, 2012

(65) Prior Publication Data

US 2012/0279633 A1    Nov. 8, 2012

Related U.S. Application Data

(63) Continuation-in-part of application No. 12/399,973, filed on Mar. 8, 2009, now Pat. No. 8,207,508.

(60) Provisional application No. 61/034,977, filed on Mar. 8, 2008.

(51) Int. Cl.
*G01N 21/64* (2006.01)

(52) U.S. Cl.
USPC .......................................... 250/458.1

(58) Field of Classification Search
USPC ....................................... 250/458.1
See application file for complete search history.

(56) References Cited

U.S. PATENT DOCUMENTS 5,225,675 A * 7/1993 O'Donnell ................... 250/302

* cited by examiner

*Primary Examiner* — David Porta
*Assistant Examiner* — Hugh H Maupin
(74) *Attorney, Agent, or Firm* — Louis L. Wu

(57) ABSTRACT

Provided are devices and methods for quantifying a surface's cleanliness relative to a contaminant. Such devices and methods may comprise and/or use a source of interrogating radiation to which the contaminant is responsive, a means for directing the interrogating radiation, a detector, and an analyzer. Radiation emitted from the source is directed by the radiation means toward an article having the surface or comprising a surface cleaner that may hold the contaminant. The detector detects radiation from the article produced in response to the interrogating radiation by the contaminant, e.g., fluorescent or phosphorescent radiation, and generate a corresponding signal that is compared by the analyzer relative to an electronic standard that corresponds to the surface in an acceptably clean state so as to quantify the surface's cleanliness.

20 Claims, 7 Drawing Sheets

DEVICE AND METHOD FOR QUANTIFYING A SURFACE'S CLEANLINESS

CROSS REFERENCE TO RELATED APPLICATIONS

This application is a continuation-in-part (CIP) of U.S. patent application Ser. No. 12/399,973, entitled "Device and Method for Quantifying a Surface's Cleanliness," filed Mar. 8, 2009, now U.S. Pat. No. 8,207,508 by inventor John L. Lawless, allowed, which claims priority to U.S. Provisional Application Ser. No. 61/034,977, entitled "Device and Method for Quantifying a Surface's Cleanliness," filed on Mar. 8, 2008, by inventor John L. Lawless, the disclosures of which are hereby incorporated by reference in their entirety.

BACKGROUND

1. Technical Field

The present invention generally relates to devices and methods for quantifying a surface's cleanliness. In particular, the invention relates to such and methods that direct interrogating radiation toward a surface or a surface cleaner detecting radiation from the surface or the surface cleaner produced in response to the interrogating radiation.

2. Related Art

In numerous industries, surface contamination and measurement thereof are issues of utmost importance. For example, the manufacturing of painted metal articles may require metal parts to be cut before they are painted. Often, cutting processes leave oil residues on the metal parts. Oil residues may interfere with the adhesion of paint to the metal parts. Thus, as a quality control measure, the metal parts are typically cleaned after they are cut before they are painted to ensure that the paint does not peel away from the parts.

Surface purity is also an important issue in facilities that handle reactive chemicals. For example, after each run, cleanliness of pharmaceutical reactors must be validated before they are returned to use. Similarly, in environments that are repeatedly exposed to large quantities of fluorine, e.g., reaction chambers of chemical lasers that use hydrogen fluoride and/or deuterium fluoride, cleanliness is a critical issue since the fluorine compounds may be highly reactive in nature and may explode upon contact with contaminants.

Furthermore, exacting standards of surface cleanliness are required in various aerospace and astronautic applications. For example, space shuttles use large quantities of pure oxygen which explodes upon contact with hydrocarbon impurities. All surfaces exposed to pure oxygen must be cleaned to exacting standards. Similarly, many parts on modern airplanes and helicopters, particularly nonmetal articles made with epoxy composites, must be cleaned before they are bonded to each other. Otherwise, catastrophic results may occur due to adhesion failure.

In response to these concerns, various industries have come up with cleaning protocols and standards to assure address cleanliness issues. Both aerospace and semiconductor industries have found it essential to control contamination through the use of clean rooms. Clean room standards have now been adopted by the International Organization for Standardization (ISO) that set forth contamination per unit volume. As defined by ISO 14644-2, "class 100" means that there are less than 100 particles of 0.5 µm or larger in a cubic foot.

In addition, standards have been developed that set forth contamination per unit surface area. For surface contamination, standard MIL-STD-1246C (or equivalently IEST-STD-1246C) has been developed to define a surface contaminated with less than 1 microgram per cm$^2$ of oil to be "Level A." If a particle count is small enough to meet level 100, then is said to be level 100-A.

Nevertheless, there are a number of shortcomings associated with known protocols and standard methods for determining the cleanliness of a surface. For example, in nonvolatile residue (NVR) testing, a surface cleaner, e.g., a sheet of filter paper or (preferably non-shredding) tissue wipe, may be used to wipe down a surface. The cleaner may then be sent away to a NVR testing facility where it is washed with a suitable solvent to extract any contaminants the may be present on the tissue. Then, the solvent is left to evaporate in a preweighed weighing dish. The resulting added mass is reported in milligrams per square foot of surface area.

NVR testing is suboptimal for numerous reasons. In general, NVR testing is procedurally difficult. Such testing may also be time consuming. When the NVR testing facility is remotely located relative to the location of the surface to be tested, it may take days to receive results of such testing. To ensure that the surface does not become contaminated by the time NVR test results arrive, the surface may have to be isolated and stored in controlled environments such as clean rooms, thereby increasing the costs associated with cleanliness validation. Furthermore, such testing results occasionally in gross errors.

While in situ testing techniques are available, they are generally qualitative rather than quantitative in nature. For example, black-light (wavelength 366 nm) monitoring of large-scale bonding surface for contamination has been described in Chawla, "Measuring Surface Cleanliness," Precision Cleaning, pages 11-15, June, 1997 (accessed from http://www.p2pays.org/ref/02/01816.htm on Mar. 2, 2009, hereinafter "Chawla"). However, such techniques are accompanies with numerous limitations. In general, black light has not been known to be useful for detecting contaminants such as light machine and tapping oils, hydraulic oil and silicone room-temperature vulcanizer (RTV) compounds that do not fluoresce strongly at low levels of contamination. In addition, black-light inspection is subjective, not quantitative and creates no record that is analyzable relative to accepted electronic standards.

In addition, fluorescent and phosphorescent methods to determine the cleanliness of metallic surfaces may not be useful for nonmetallic surfaces. For example, metallic surfaces generally do not fluorescence, whereas many composite materials used in aerospace and astronautic applications do. In some instances, the intensity of fluorescent background radiation may overwhelm the intensity of signal generated for contaminant detection.

The few quantitative technologies that have been used to determine the cleanliness of a surface other than for biohazards such as food and drink contamination are generally limited in nature. For example, U.S. Pat. No. 6,310,348 to Melling et al. describes an accessory for an FTIR spectrometer comprises fiber-optic cables that may be used to detect and characterize quantifying thin films on reflective surfaces for cleaning validation applications. Such spectrometry based technologies require a reflective surface and the precision relative placement the accessories relative to the surface so as to achieve a "grazing angle" for maximum sensitivity.

Thus, opportunities exist to provide alternatives and improvements to known protocols and technologies for evaluating the cleanliness of a surface. There exist further opportunities to provide improved technologies for evaluating the cleanliness of a surface despite the surface being comprised of a material that may produce potentially interfering background radiation, resulting in the generation of interfering noise, e.g., of a fluorescent and/or phosphorescent nature.

SUMMARY OF THE INVENTION

In a first embodiment, the invention provides devices for quantifying a surface's cleanliness relative to a contaminant. The devices of the invention include a source of interrogating radiation to which the contaminant is responsive, a means for directing the interrogating radiation, a detector, and an analyzer. Radiation emitted from the source is directed by the radiation means toward a nonmetallic article having the surface or comprising a surface cleaner that may hold the contaminant. The detector is positioned to detect radiation from the article produced in response to the interrogating radiation by the contaminant, e.g., fluorescent or phosphorescent radiation. Once radiation is detected, the detector generates a signal that corresponds to the detected radiation. Optionally, the detector may further be responsive to radiation reflected from or transmitted by the surface or the surface cleaner. Then, the analyzer compares the signal from the detector relative to an electronic standard unrelated to the detection of pathogens and other biohazards that corresponds to the surface in an acceptably clean state so as to quantify the surface's cleanliness. Further optionally, surface fluorescence or phosphorescence may be advantageously used to improve the performance of the invention.

In another embodiment, methods are provided for quantifying a surface's cleanliness relative to a contaminant. The methods involve generating interrogating radiation to which the contaminant is responsive. The interrogating radiation is directed toward a nonmetallic article having the surface or comprising a surface cleaner, e.g., a sheet of filter paper and/or a cleaning fluid, that may hold the contaminant from the surface. Radiation from the article produced in response to the interrogating radiation by the contaminant is detected. In turn, a signal is generated that corresponds to the detected radiation. The signal from the detector is compared to a standard unrelated to biohazard detection that corresponds to the surface in an acceptably clean state so as to quantify the surface's cleanliness. Optionally, the method may be used to quantify a surface's bondability relative to at least one bondability parameter, e.g., surface roughness.

In a further embodiment, a method is provided for bonding a plurality of surfaces that may or may not be contaminated by at least one surface contaminant. The method generally involves quantify the at least one surfaces' cleanliness using the above-described method and applying an adhesive between the surfaces so as to bond the surfaces.

The invention may be used to quantifying a surface's cleanliness relative to any of a number of contaminants using interrogating radiation of various wavelengths. For example, the surface contaminant may comprise particulate matter and/or organic matter such as a hydrocarbon. In addition, the interrogating radiation may be of ultraviolet, infrared and/or visible wavelengths. Monochromatic radiation and/or radiation including a range of wavelengths may be used.

Different types of hardware may be employed that are suitable for handheld use. For example, the detector may include, a charge-couple device (CCD) camera and/or a photodiode. In addition, the analyzer may include a microelectronic device and/or a computer port interface. When the invention is used to quantify a surface's cleanliness, a contaminant concentration per surface area and/or a particulate count may be calculated. If the calculation reveals that the surface is acceptably clean, the surface may be placed in a contaminant sensitive environment, such as an oxygen facility or an environment that allows the surface to be placed in contact with a halogen such as fluorine. In addition or in the alternative, the surface may be bonded to another surface, e.g., one that comprises epoxy.

Additional embodiments of the invention will be apparent from the disclosure contained herein.

Figure 1:
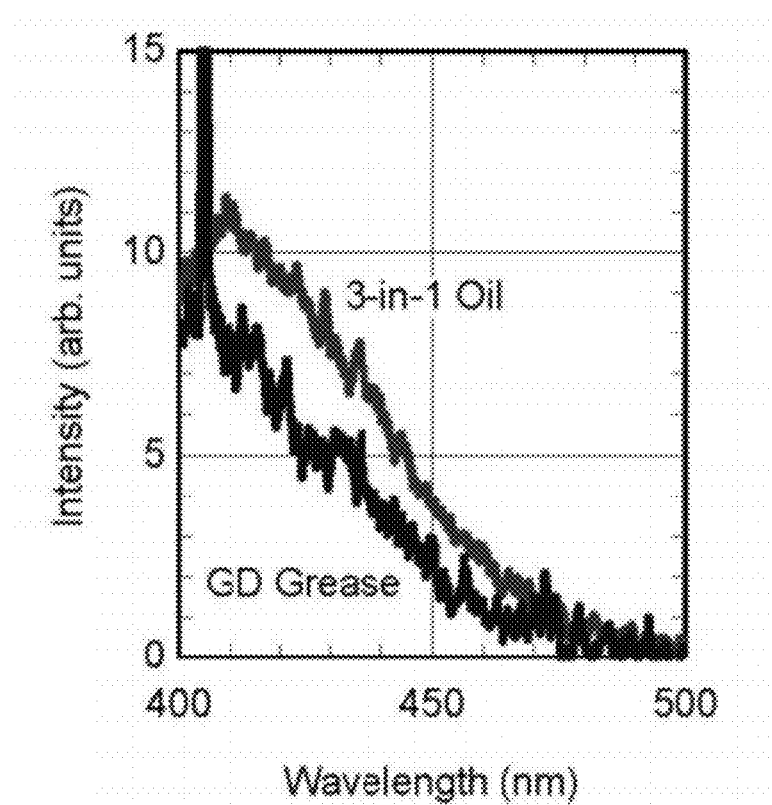
FIG. 1 graphically illustrates differences in fluorescence behavior of common organic contaminants, i.e., 3-in-1 oil and household (garage door) grease, under ultraviolet (UV) light generated by a mercury lamp. The peak at 405 nm is from the mercury lamp.

The invention and aspects thereof shown in the figures may not necessarily be depicted to scale, and certain dimensions may be exaggerated for clarity of presentation.

DETAILED DESCRIPTION OF THE INVENTION

Definitions and Overview

Before describing the invention in detail, it must be noted that, as used in this specification and the appended claims, the singular forms "a," "an," and "the" include plural referents unless the context clearly dictates otherwise. Thus, for example, reference to "a contaminant" includes one or more contaminants, reference to "a parameter relevant to bondability" includes a single parameter relevant to bondability as well as a collection of parameters relevant to bondability, reference to "a wavelength" includes a single wavelength as well as a range of wavelengths, and the like.

In describing and claiming the present invention, the following terminology will be used in accordance with the definitions set out below.

The term "black light" as used herein refers to radiation invisible to the naked human eye, typically of ultraviolet (UV) or infrared (IR) wavelengths, that causes fluorescent materials to emit radiation of a different wavelength, e.g., visible light. In certain specific instances, black light refers to radiation emitted by economical gas light bulbs having a peak intensity wavelength of about 366 nm radiation, which, as discussed Chawla, cannot be used to detect machine oil.

The term "cleanliness" as in a "surface's cleanliness relative to a contaminant" is used in its ordinary sense, and refers the surface's freedom from the contaminant, e.g., foreign matter or pollution. As a related matter, the term "contaminant" as in "surface contaminant" is also used in its ordinary sense and refers to matter that renders the surface impure or unclean by its presence or contact.

The terms "fluorescence" and "fluorescent radiation" are used herein in their ordinary sense and refer to the emission of electromagnetic radiation produced by a substance as a consequence of the absorption of incident (interrogating) radiation and persisting only a short time after the incident radiation ceases to stimulate the substance. Unlike "reflected" or "transmitted" fluorescent radiation typically has a longer wavelength than its corresponding incident radiation.

The terms "phosphorescence" and "phosphorescent radiation" are used herein in their ordinary sense and refer to the emission of electromagnetic radiation produced for some time following exposure to and removal of incident (interrogating) radiation, typically at a temperature below that of incandescence.

The term "signal" is used herein in its ordinary sense and refers, for example, to an impulse, fluctuating electric quantity, such as voltage, current, or electric field strength, or a variable parameter, such as radiation spectra intensities, whose existence and/or variations represent coded information.

As a related matter, the term "noise" is also used in its ordinary sense and refers to any disturbance, random or otherwise, that obscures or reduces the clarity of a signal. For example, systemic unwanted contributions to a signal that interfere with or confound decoding of a signal is also considered noise, even if the contributions are not random.

In general, the invention provides devices and methods for quantifying a surface's cleanliness relative to a contaminant. The invention operates by using radiation to which the contaminant is responsive to interrogate the surface whose cleanliness is to be quantified or to interrogate a surface cleaner that may hold contaminant from the surface. In response to the interrogating radiation, the contaminant may produce a detectable response, e.g., fluorescent or phosphorescent radiation, which may be detected and converted into a signal. The signal is then compared to an electronic standard that corresponds to the surface in an acceptably clean state so as to quantify the surface's cleanliness.

In some instances, the invention may take the form of a hand-held field-portable instrument that is able to quickly and easily read contamination levels traceable to precision cleaning standards, e.g., U.S. Military Standard MIL-STD-1246C promulgated by the U.S. Department of Defense. Such instruments may provide readings for both the molecular contamination level, such as organic matter in the form of hydrocarbon oils, grease, etc., and particulate contamination level, such as grit and dust. Such instruments may further measure surface conditions, e.g., surface roughness, that may be relevant to surface bondability.

The invention may employ one or a combination of various optical techniques. For example, the invention may exploit the fluorescent and/or phosphorescent behavior of contaminants by employing interrogating radiation of appropriate ultraviolet (e.g., UV-A, UV-B, UV-C, etc.), visible, and/or infrared (e.g., near IR, short-wavelength IR, mid-wavelength IR, long-wavelength IR, Far IR, etc.) wavelengths. Such interrogating radiation may exhibit a range of wavelengths or be monochromatic in nature. As another example, the invention may exploit the fact that particulate contaminants scatter light, and a detector may be used that is responsive to reflected or transmitted radiation. By comparing signals associated with light scattering to signals associated with no light scattering, particulate matter may be quantified. As a further example, any of these techniques can be supplemented with variations on illumination (frontal illumination, edge illumination, blue, etc.). In any case, exemplary detectors that may be used with the invention include CCD arrays, miniature spectrometers, photodiodes, microelectronic devices, and the like. Optionally, devices of the invention may include an interface or so that data gathered by the analyzer may be transferred to remote computers.

The invention may be practiced via in situ measurements. In situ measurements, for example, may involve placing the inventive instrument such that the interrogating radiation is be directed toward the surface whose cleanliness is to be quantified. In such a case, spectrometer may be used to quantify molecular contamination via fluorescent intensity. In addition or in the alternative, the detector may comprise a camera or other type of imaging technology suitable for counting particulates. Care must be taken to distinguish surface-generated background noise generated versus contaminant generated signals.

Standard contamination tests may be adapted for use with the invention. One standard contamination test involves wiping a region of a predetermined area, e.g., one square foot, of the surface with a high-quality filter paper as a surface cleaner and sending the filter paper for NVR testing. Another standard test involves rinsing the surface in a surface cleaner in the form of a solvent, e.g., haloalkanes sold by DuPont under the trademark Freon®, and analyzing the surface cleaner via remote NVR testing. In either case, the inventive device may be constructed for on-site testing so as to supplement or replace remote NVR testing. Such devices may, for example, include surface cleaner holder constructed to hold a sheet of paper or a rinse fluid.

Once a surface is determined to be acceptably clean, the surface is may be ready for use. For example, the surface placed in a contaminant sensitive environment. As discussed above, the invention is particularly suited to determine whether a surface is sufficiently clean for exposure to oxygen facilities or for contact with a halogen such as fluorine. In addition, the surface may be bonded to another surface, e.g., an epoxy surface.

Contaminant Quantification

The invention employs optical means that generally conform to accepted standards of the precision cleaning industry to quantify the cleanliness of a surface. In particular, the invention employs optical technologies that represent an improvement over black-light detection practices known in the precision cleaning industry. Accordingly, some background regarding how black-light detection practices are carried out is warranted.

As alluded to above, black light has been used to provide a qualitative indication of the cleanliness of a surface. For example, known surface cleaning protocols typically involve first wiping a predetermined area of the surface with a standard two-inch diameter scientific grade filter paper. Then, the filter paper is exposed to UV radiation. If the paper is observed to exhibit fluorescence, i.e., by glowing while exposed UV radiation, additional cleaning is needed.

For certifiable results, the paper is typically sent to a specialized lab for NVR testing to quantify how much non-volatile residue was removed from the surface. NVR testing may involve rinsing the paper with a solvent to remove contaminants therefrom and quantifying contaminants in the runoff solvent. The results of NVR testing may then be used to determine whether the surface exhibits a cleanliness level that conforms to an accepted standard of cleanliness.

Considering how inaccurate human eyes are as optical instruments, that the qualitative test may serve as an initial screening technique at all is impressive. Human eyes, for example, have greatly varying sensitivity both between day and night vision and between one person and the next. Further, certain important fluorescence phenomena occurs at the blue edge of the visible spectrum and naked-eye sensitivity at either edge of visible light varies greatly from one individual to another. In short, naked-eye black-light inspection as a protocol is fraught with variability due to is subjective and qualitative nature.

In contrast, the invention provides, as an inventive embodiment, an optical instrument capable of performing quantitative black-light analysis and of creating a record that is analyzable relative to accepted electronic standards. Unlike human eyes, photodetectors are consistent and quantitative. The inventive instrument may be used to make measurements of fluorescence and, using a calibration curve, report the contamination level to the user. In addition, the fluorescence spectra of the contaminants can be quantified, leading to identification of individual contaminant species. With the addition of more excitation sources, covering the wavelength spectrum from blue to UV-A, further discrimination among contaminant species would be possible.

The accuracy the invention may be independently verified using known techniques, e.g., via NVR testing techniques. For example, the invention may be used first to quantify a surface's cleanliness by directly interrogating the surface. Then, the surface may be wiped with filter paper, and the invention may be used to quantify the cleanliness of filter paper. In turn, the paper may be sent for NVR testing to verify the result obtained by the practice of the invention. In this way, the accuracy and precision of the invention may be calibrated and/or verified using industry standards.

To demonstrate the feasibility of such an approach the fluorescence spectra of two different hydrocarbon contaminants were measured. A long-wave black-light lamp was used to illuminate filter paper specimen from Whatman Inc. (Piscataway, N.J.) holding different contaminants. One specimen was contaminated with 3-in-1 (SAE-20) oil, and another was contaminated with a common household (garage door) grease. A detector was used to collect fluorescence spectra and the output was plotted. The fluorescence spectra are shown in FIG. 1.

As expected, the fluorescence yields of the contaminants were fairly similar. Both glow at the blue end of the visible spectrum. This is not surprising because oils and greases typically belong to the hydrocarbon family and have similar chemical structure. There are significant differences, however. For example, the oil appears to peak at a longer wavelength than the grease. The human eye could never detect such a difference. Such difference may be exploited to help improve the calibration of the analyzer and, possibly, to distinguish different types of identify the contaminants.

The invention may also be used to quantify particulate contaminants. This can be done using any of the sampling methods described above. For example, particulates may be spread out on a surface, illuminated, and imaged (e.g., via CCD camera). Then, software may be used to provide a particle count.

Optionally, the particles may be sized. Large particle can be sized by determining the number of pixels needed to capture their entireties. Small particles can be sized by intensity of light they reflect. The relationship between intensity and size can be established by using commercially available particles of known size as a calibration standard. For example, spherical microparticles with calibrated sizes traceable to the National Institute of Standards and Technology (NIST) are available from Thermo Fisher Scientific Inc. (Waltham, Mass.), formerly Duke Scientific.

Certain techniques may be used to enhance particle quantification. For example, edge illumination techniques may serve to highlight the particle for counting and/or counting, even if the particles are the same color as the surface on which they lie. Regardless of color, a particle will scatter light due to irregular discontinuities in the index of refraction that characterize a particle as opposed to a clean surface.

Other illumination methods can also be used to advantage as well. For example, illumination with different wavelengths can help determine the particles composition. When exposed to UV radiation, organic particles may fluoresce.

Exemplary Instrumentation

Figure 2:
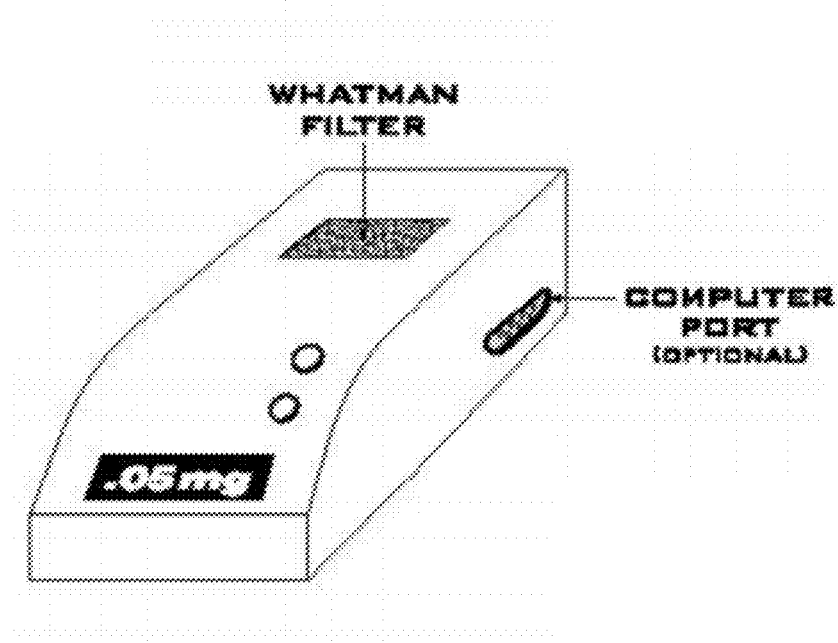
FIG. 2 depicts an exemplary embodiment of the invention in the form of a small hand-held instrument that can quantitatively read fluorescence under black light.

In certain embodiments, the invention may provide a small hand-held battery-powered instrument. FIG. 2 depicts an exemplary embodiment of the invention in the form of a small hand-held battery powered instrument that can quantitatively read fluorescence under black light. Optionally, the battery (not shown) may be replaced or supplemented with an AC power supply. As shown, the instrument houses a sample cleaner holder adapted to a piece of Whatman filter paper, a display the shows analytical results in units of mass, and an optional computer port.

Figure 3:
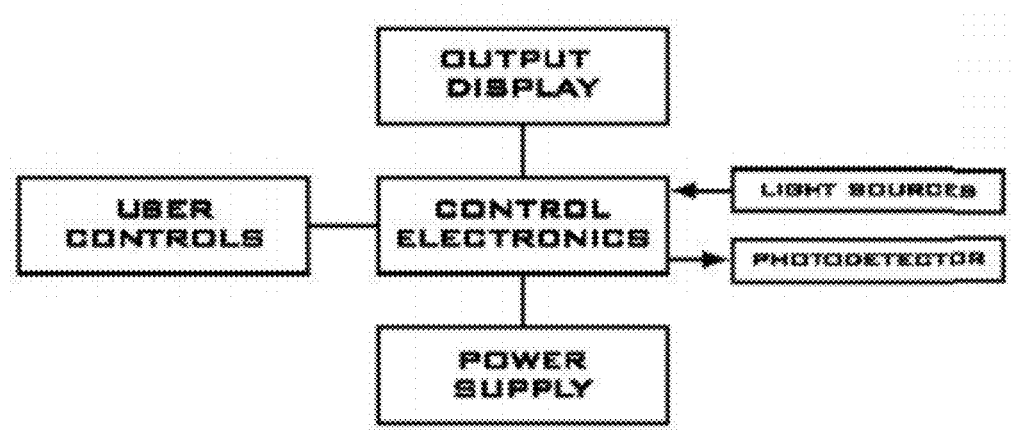
FIG. 3 shows a block diagram of an exemplary instrument of the invention.

FIG. 3 shows a block diagram the instrument depicted in n FIG. 2. User controls may be interfaced with control electronics, which communicate electrically with the output display and a power supply. The operation of control electronics may be triggered in part by the activation of interrogating radiation sources, which, in turn, may activate the photodetector.

Figure 4:
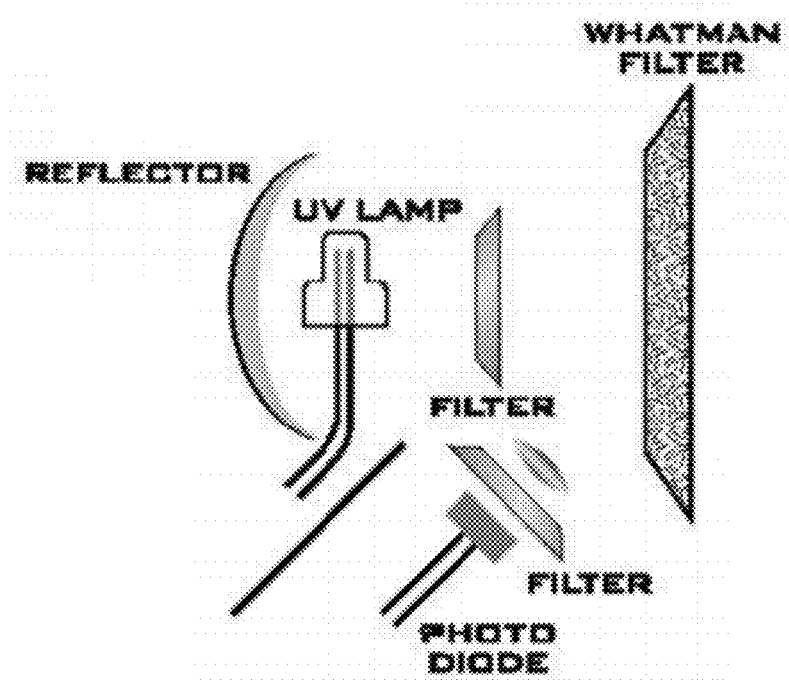
FIG. 4 shows in schematic view an exemplary setup in which a UV light source is used to illuminate a contaminated specimen of Whatman filter paper, and a photodiode is used to detect fluorescence produced as a result.

FIG. 4 shows in schematic view an exemplary setup in which a UV light source is used to illuminate a contaminated specimen of Whatman paper and a photodiode is used to detect fluorescence produced as a result. The setup is particularly suited for quantifying molecular contaminants. As shown, the UV light source may take the form of a mercury lamp in combination with a reflector that serves to direct the radiation from the mercury lamp toward the specimen. An optical filter is interposed between the lamp and the specimen so that visible light is prevented from reaching the specimen. Once the filtered UV light reaches the specimen, contaminants held thereby may exhibit fluorescent behavior. Any fluorescent radiation produced may be collected by a lens and quantified by a photodiode. Optionally, reflected and other stray UV radiation may be blocked from reaching the photodiode by a UV-blocking filter interposed between the specimen and the photodiode. An additional photodiode (not shown) may be used to measure the UV intensity of the lamp for purposes of calibration.

It should be noted that the invention is not limited to black-light radiation technologies, as described in Chawla in which black-light sources are used having a peak intensity wavelength of about 366 nm. Commercially available technology has improved to the point that, mercury lamps, properly powered and filtered, are now also capable of emitting at 253.65 nm and several other wavelengths. This enables clear observation of many contaminants that were previously thought at the time of Chawla unobservable with black-light techniques. Modern light emitting diode (LED) sources offer many choices with emission peaks from 250 nm to 400 nm.

Figure 5:
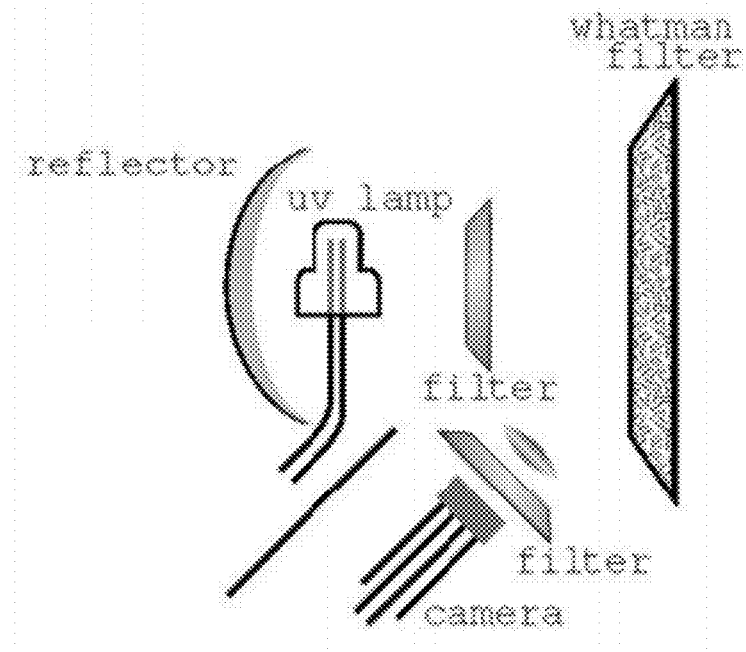
FIG. 5 shows in schematic view a variant of the setup shown in FIG. 4 in which the photodiode is replaced by a CCD camera.

As discussed above, a CCD (or CMOS) camera may be used to image particulate contamination. A series of images may be taken under different illumination schemes. These images may then be analyzed by a microprocessor to count and/or size particles. As shown in FIG. 5, a variant of the setup shown in FIG. 4 may be used to carryout such particle quantification. Persons of ordinary skill in the art would recognize that the invention may employ a detection scheme that employs both photodiodes and CCD cameras to quantify both molecular and particulate contaminants.

As discussed above, spectral information obtained through the use of the invention may be employed in a calibration context and/or to help type of contaminant. In some instances, quasi-spectral information may be obtained by employing multiple photodiodes, each with a different spectral filter or a photodiode array with a linear variable filter. More complete spectral information may be obtained by using miniature spectrometer as the detector of the invention. In either case, quantitative measurements of fluorescence may be made at different wavelengths. The ratios of the intensities at the different wavelengths could be correlated contaminant composition. The difference in the spectra of different hydrocarbon compounds shown in FIG. 2 indicates the potential for this approach.

Further information may be obtained from the decay times of the fluorescent or phosphorescent radiation. Thus, in some embodiments, it may be preferred that the invention employ one or more light sources with rapid response performance capabilities, e.g., with capability for rapid turn on and turn off. This has two advantages. First, since sensitivity to minute quantities of contamination is important, the use of lock-in amplifier techniques can help improve signal-to-noise ratio and hence sensitivity. This typically optimizes at a flashing rate of 1 kHz to 50 kHz. Secondly, if the light source turns off quickly, it is possibly to measure or infer the fluorescent or phosphorescent decay time of the contaminant. This can contain information about the type of contaminant and/or its environment. This usually requires turn-off times of no more than a microsecond. While turn off times may limit flashing rates, flashing rates, may vary with different types of light sources. In some instances, the invention may involve on-off flashing rates of megahertz and above. Alternative, the invention may employ Nd:YAG lasers having turn-off times measured in nanoseconds. This may correspond to flashing rates limited to kilohertz.

Furthermore, infrared spectroscopic techniques may also be used to improve the quantitative aspects of invention. It is well known that infrared spectroscopy techniques have been likened to a "molecular fingerprinting." Traditional infrared analysis has required expensive instruments, special windows, and cryogenic cooling. Recent advances in semiconductor technology, however, enable practical affordable instruments using conventional optical materials that perform spectroscopy (at room temperature) in the near-infrared. Commercially packaged miniature spectrometers are now available in for near-IR applications.

Figure 6:
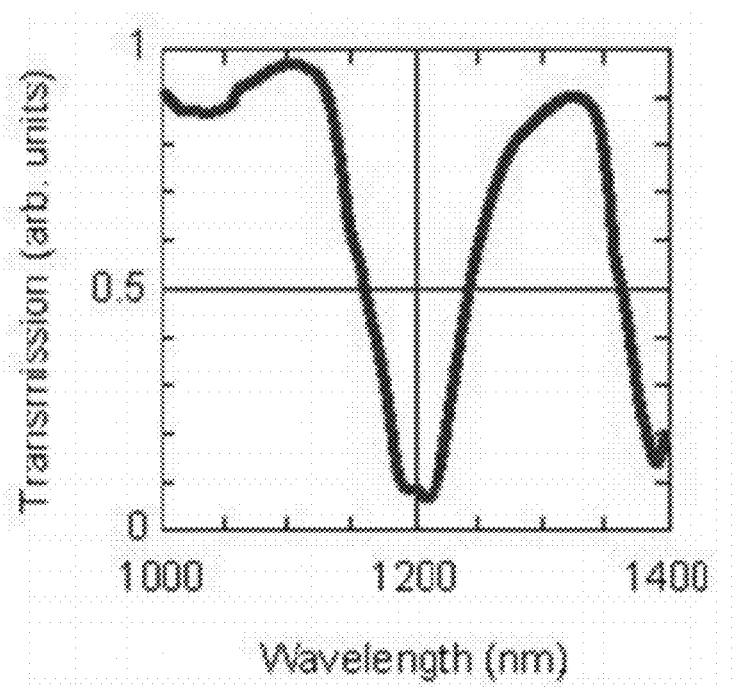
FIG. 6 graphically illustrates the transmission of the IR spectrum for 3-in-1 oil as plotted against wavelength FIG. 7 graphically illustrates the near-IR reflection spectrum of a specimen of oil-contaminated filter paper relative to the reflection spectrum of a clean (uncontaminated) specimen.

To illustrate the nature of near-IR technology, experiments were performed on a sample of pure 3-in-1 (SAE 20) motor oil, a typical repair shop contaminant. Light transmission was measured through the oil. FIG. 6 graphically illustrates transmission spectra of the 3-in-1 oil sample as plotted against wavelength. Notably, the oil sample shows strong absorption (low transmission) behavior near 1200 nm and 1400 nm. These absorption peaks (among others not shown) are common to petroleum products ranging from oils to gasolines. By studying the precise shapes and relative heights of the peaks, it is possible to determine nearly all properties of oil or gasoline from viscosity to cloud point.

Figure 7:
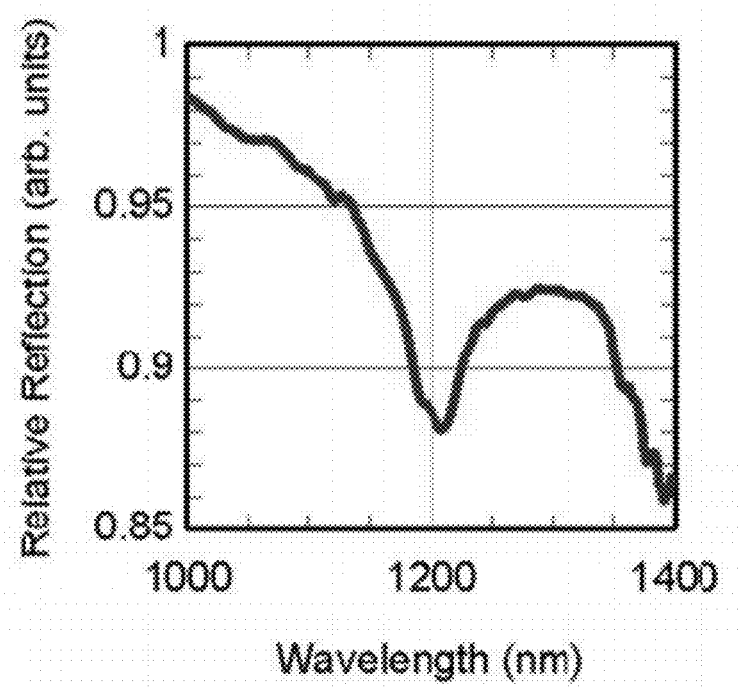

To see whether the invention may be applied to bondability applications, reflected near-IR radiation from a Whatman filter paper specimen was measured under both clean and contaminated conditions. 3-in-1 oil was used as the contaminant. As shown in FIG. 7, the contaminant oil reduced reflected radation at several wavelengths. The spectral features at 1200 nm and 1400 nm match those of the pure oil. In particular, the spectral feature at 1200 nm regions exhibits a double peak with one peak a little stronger than the other. A similar double peak can also be seen for the spectral plot at 1200 nm for pure oil in FIG. 6. Accordingly, it is clear that the invention may be used to quantify oil contamination a Whatman filter using near infrared spectroscopy.

Figure 8:
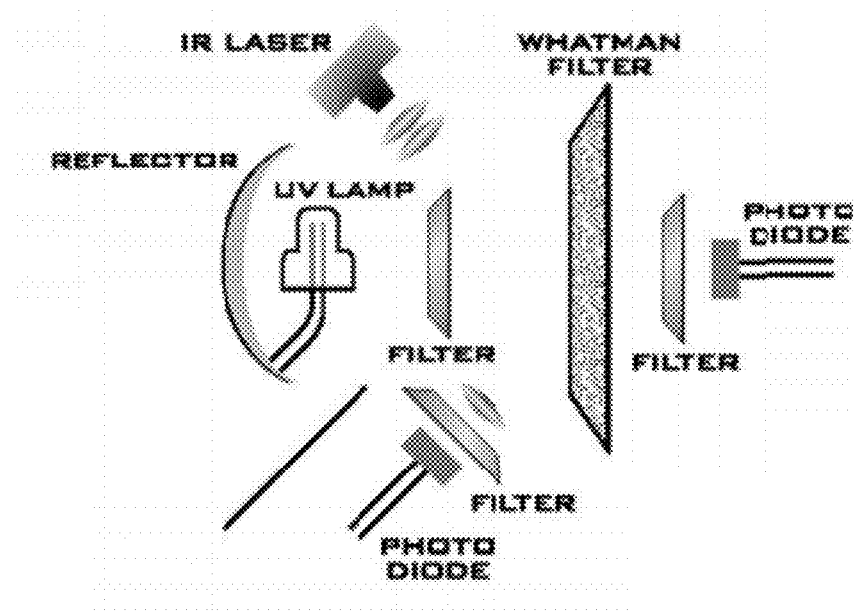
FIG. 8 shows in schematic view a variant of the setup shown in FIG. 4 in which an IR laser and an additional photodiode are added to provide improve accuracy.
Figure 9:
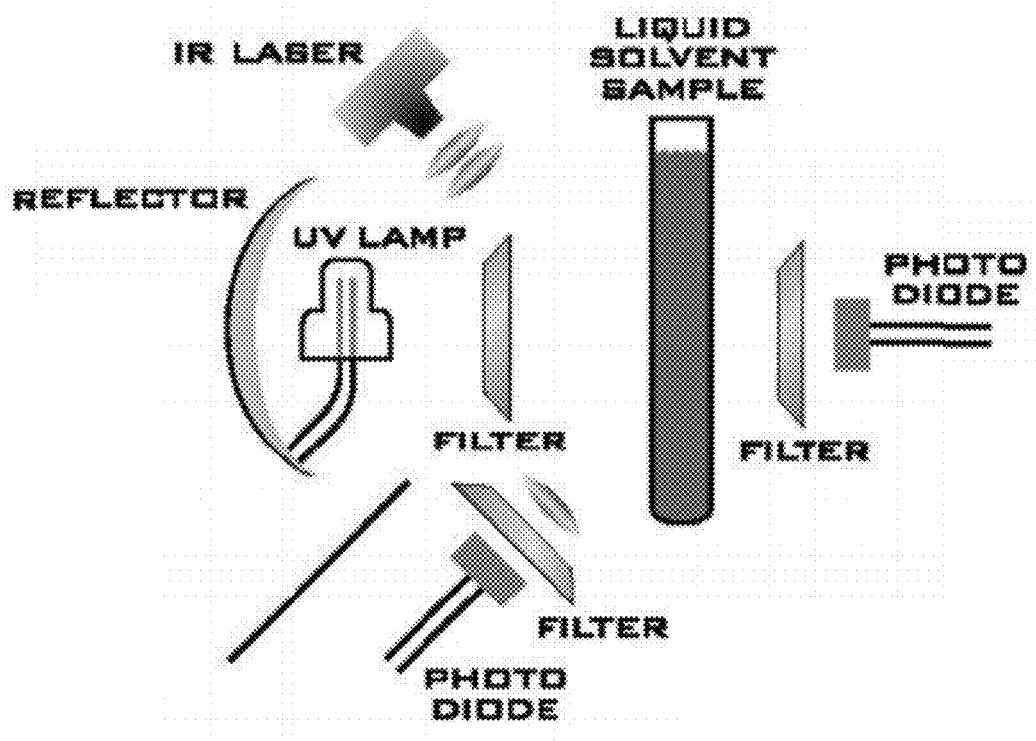
FIG. 9 shows in schematic view a variant of the setup shown in FIG. 8 except that the paper specimen has been replaced with a liquid solvent sample.

Certain infrared technology may be used to enhance in the inventive instrument. For example, FIG. 8 shows in schematic view a variant of the setup shown in FIG. 4 in which an IR laser and an additional photodiode are added to provide improve accuracy. The setup operates in a manner similar to that depicted in FIG. 4 except that the IR laser and additional photodiode may be used to carry out spectroscopic measurements to supplement the fluorescence quantification capabilities of the invention. In some instances, the laser may be tuned over its wavelength range to obtain spectral information that may distinguish further the different kinds of contaminants. For example, near-IR spectra may be used to infer viscosity or SAE number FIG. 9 shows in schematic view a variant of the setup shown in FIG. 8 except that the paper specimen has been replaced with a liquid solvent sample. Such a setup may be used in rinse testing applications. More specifically, smaller parts or rough surfaces having a form factor unfriendly to wiping may benefit from such a setup. With this setup, black-light fluorescence may be measured directly from the solvent wash and while a CCD camera inspects for particles in the solvent.

Other instrumentation variants are possible. For example, the invention may employ detectors other than CCD cameras and photodiodes. In some instance, photomultiplier tubes and avalanche photodiodes may be used.

Noise and Calibration Issues

To ensure adequate precision, accuracy and reliability, the invention, in some embodiments, may include enhanced means for to enhance the signal-to-noise ratio associated with the invention. As discussed above, the invention may include a detector to detect for radiation fluorescently produced by surface contamination as a result of exposure to interrogating radiation. Then, the signal associated with contaminant-produced fluorescence is compared with an electronic standard that corresponds to the surface in an acceptably clean state. However, such a detector may detect additional radiation (noise) from other sources as well.

For example, in an embodiment of the invention as described above that involves detecting radiation fluorescently produced by a surface contaminant, the detector may additionally detect radiation that has been reflected by the surface and/or contaminant. In a simple case, when the interrogating radiation starts out spectrally pure or substantially monochromatic, e.g., as emerging from a laser, the light filters and optics along the path of travel may add their own fluorescence. Thus, while some reflected radiation may be of the same wavelength as the spectrally pure the interrogating radiation, some of the interrogating radiation that ends up reaching the detector may be of the same wavelength as the contaminant-produced fluorescent radiation.

Parenthetically, it should be noted that the above described light filters and optics discussed above are almost never flawless in performance. For example, while filters are constructed to block undesirable wavelengths, some undesirable wavelengths may be transmitted to a small but non-negligible degree. Also, as discussed above, many light filters themselves fluoresce. As a result, false signals, i.e., noise, may be generated that are strong enough to interfere with observation of fluorescence from weak contamination.

In a more complicated case, if the source of interrogating radiation is a gas lamp or a LED, the initially generated radiation itself will exhibit a complicated spectrum. In particular, LEDs are known to exhibit broad spectral tails which may interfere with the measurement of weak contaminant-produced fluorescence. In addition, many commercially available ultraviolet LEDs are made of materials which themselves add fluorescence peaks to LED output. Thus, the interrogation radiation itself may provide a potential source of noise.

Another potential source of noise is the surface on which the contaminant may be held. That is, the surface holding the contaminant may fluoresce when exposed to interrogating radiation. Although clean metal surfaces generally do not fluoresce, plastics and composites do. In particular, graphite composites that are becoming increasing popular in aircraft designs also tend to fluoresce.

In any case, a successful implementation of the above-described inventive embodiment should involve separation of signal generated as a result of contaminant-produced fluorescence from noise generated by any of a number of sources.

Figure 10:
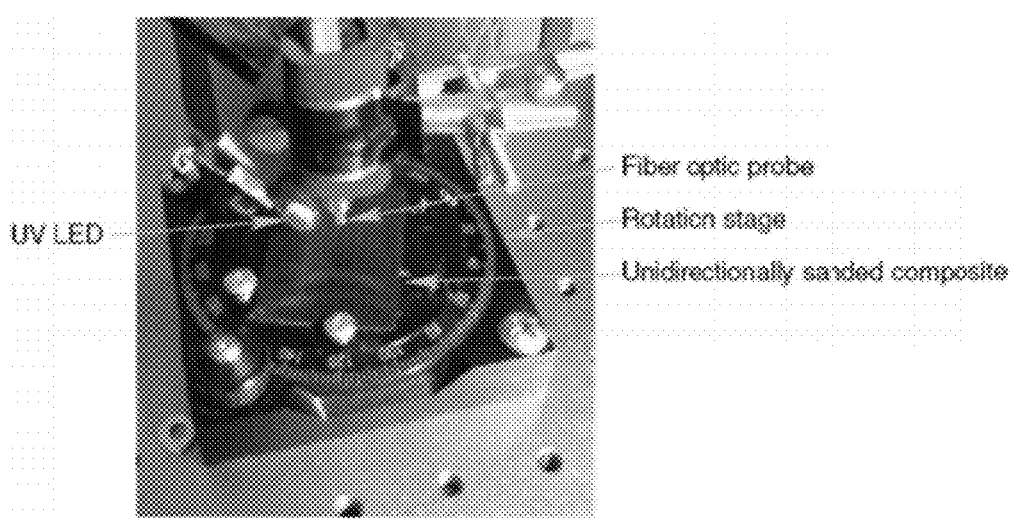
FIG. 10 is a photograph of an exemplary laboratory apparatus that may be used to vary the orientation of a sample surface relative to a radiation source and a detector.

It should be noted that efforts in separating signal from noise may be complicated by the fact that the intensity of the radiation reflected from a sample surface and reaching a detector can vary widely depending on surface conditions, e.g., roughness, orientation, etc. This has been demonstrated using laboratory apparatus shown in FIG. 10. The laboratory apparatus includes a LED which directs UV radiation onto a graphite fiber composite sample having a sanded surface. Radiation from the sanded surface is collected by the fiber optic probe and delivered to a monochromator. The composite is attached to an optical stage that permits easy rotation of the sample.

Figure 11:
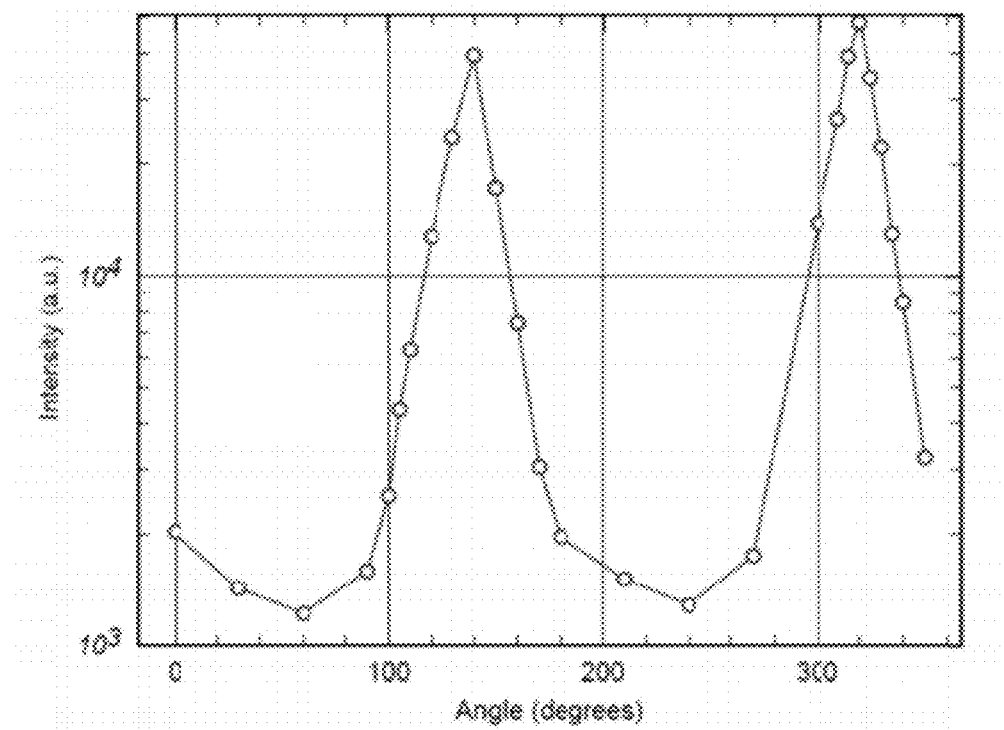
FIG. 11 is a plot that graphically illustrates how the intensity of reflected light may vary as the orientation of a sample surface is varied relative to a radiation source and a detector.

As shown in FIG. 11, the intensity of the reflected light varies as the optical stage is rotated. The minimum and maximum intensity of the reflected varies by nearly a factor of 100 as the angle of the incident radiation relative to the orientation of the sample is changed. As discussed above, the sample was sanded before testing. As a result, grooves were formed on the sample surface. Depending on the orientation of the grooves, the reflected radiation may be directed toward or away from the optical collection fiber. Accordingly, the large change in observed radiation intensity can be attributed to sample surface conditions produced as a result of sanding. As surfaces are commonly sanded prior to bonding, such intensity variation problems should be regarded as typical rather than exceptional.

Another factor that may complicate the practice of the invention relates to the presence of contaminant of the surface. The presence of such surface contaminants may also change the intensity of reflected radiation. In particular, the amount distribution of contaminant on a surface may affect how radiation is reflected.

In sum, one needs to be able to identify the contaminant fluorescence even with strong masking/interfering radiation, e.g., from target surface fluorescence. Such masking/interfering radiation may vary in intensity to wildly unpredictable degree, e.g., on the order to magnitude of source light reflectance.

To address the above-discussed variability in signal-to-noise ratio, a multistep step calibration process may be used to generate one or more calibration spectra. As an initial matter, scattered radiation may be measured from a clean metal surface. This step provides a baseline measure of the spectrum of the interrogating radiation that includes any fluorescence from optical components along the optical path before the radiation reaches the article holding the contaminant. Then, a second scattered radiation measurement may be taken at a first angle from a clean area of the surface of the article holding the contaminant. The second scatter radiation measurement should contain contributions associated with the baseline measurement plus contributions associated with clean surface fluorescence at the first angle. Then, a third scattered radiation measurement may be taken at a second angle from the clean area of the surface, wherein the second angle differs from the first angle. The third scattered radiation measurement should contain contributions associated with the baseline measurement plus contributions associated with clean surface fluorescence at the second angle.

It is possible that one of second and third measurements, as discussed above, may involve excessively intense reflected radiation. As a result, it may not be possible to identify with sufficient accuracy surface fluorescence via one of the second and third measurements. Thus, care should be taken to choose an incident angle appropriate to the sanding technique. With appropriate care, surface fluorescence can be identified and separated from interfering radiation, e.g., the source spectrum. Optionally, additional measurement may be carried out at different angles to account for different types of surface conditions, e.g., resulting from unidirectional, bidirectional, or random sanding techniques.

In any case, measurements of surface contamination may generally be taken at an unknown angle. By comparing the measured spectrum against a combination of one or more calibration spectra, the contaminant signal can be separated and identified. (In the event that an unfortunate angle is chosen at which reflectance overwhelms fluorescence, that can be identified and reported also.)

Figure 12:
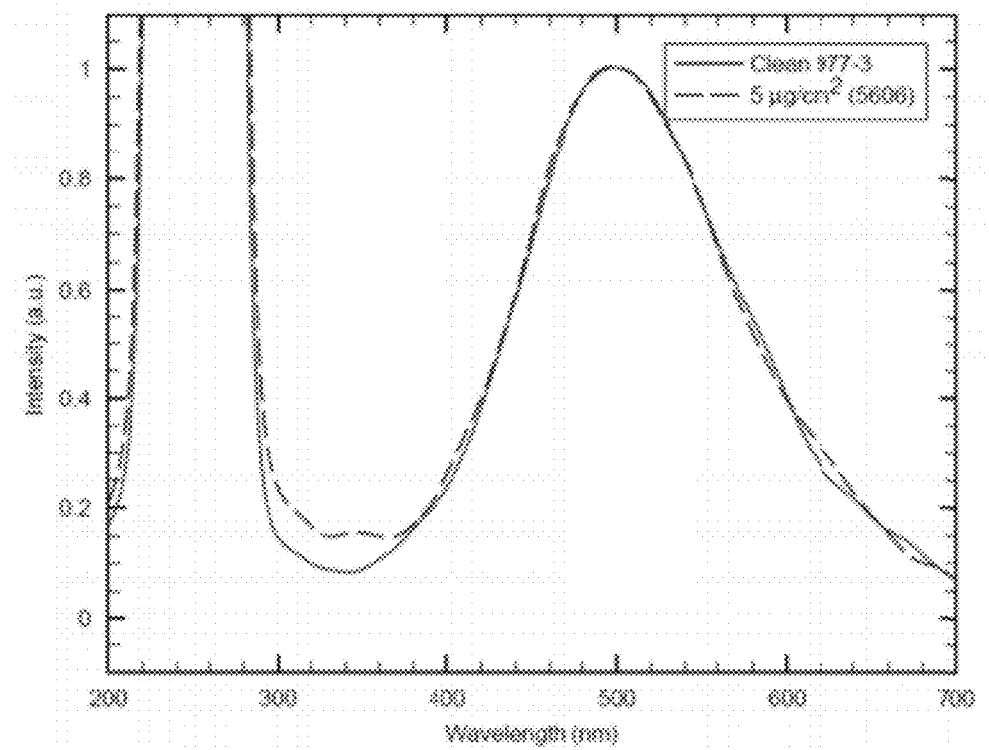
FIG. 12 plots a spectral curve associated with a first contaminant against a calibration spectral curve.

FIG. 12 depicts exemplary spectra curves associated with the invention. One spectral curve represents scattered radiation signal from a graphite composite surface (IM7/977-2) contaminated with a hydraulic fluid (MIL PRF 5606) at the level of 5 microgram/cm$^2$. The other spectral curve represents a combination of the calibration curves. The contaminant signal is clear even though the reflected light and composite fluorescence signals are both strong and overlap with the contaminant signal.

Figure 13:
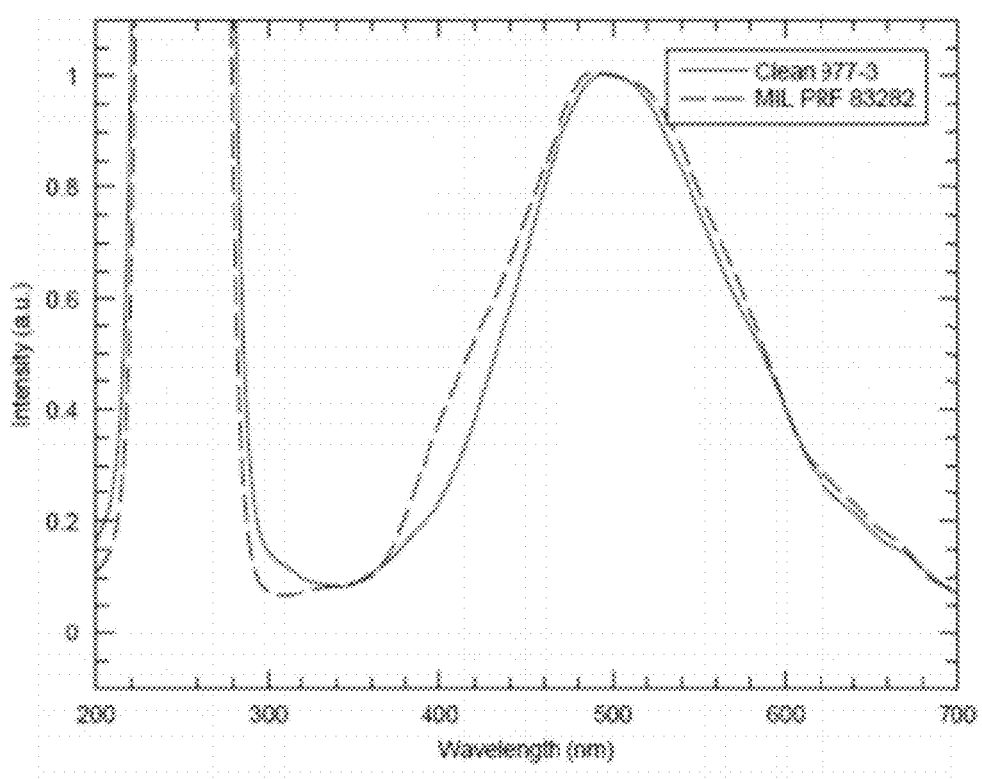
FIG. 13 plots a spectral curve associated with a second contaminant against a calibration spectral curve.

A similar plot for a different contaminant is shown in FIG. 13. As shown, the contaminant exhibits characteristic fluorescence peaks near 312 and 400 nm. The plot shows that it is possible to identify the characteristic fluorescence peaks despite spectral overlap with stronger signals from the source and the target surface.

Thus, the invention represents a novel and nonobvious improvement to cleaning protocols that require sending samples to a specialized laboratory and waiting days for results, e.g., "NVR testing." In some embodiments, portable field instrumentation may be provided for quantifying a surface's cleanliness in a near instantaneous manner. Such instrumentation may be used to facilitate repairs on aircraft in hangers at airports or other uncontrolled environments, where the use of clean rooms or specially trained technicians is not practical.

In addition, the invention also represents a novel and nonobvious improvement to cleaning techniques requiring qualitative naked eye observations. For example, a typical young person can see a black lit 50 µm particle with the naked eye while an older person can see a 100 µm particle. With optical means as described above, even small hand-held instruments can routinely read particles down to 0.3 µm or smaller.

Furthermore, the invention represents a novel and nonobvious improvement to detection technologies whose accuracy, precision, and reliability may be compromised due to issues associated with surface conditions and background radiation. In some instances, such issues may present an opportunity for improved performance, provided that appropriate calibration techniques are carried out.

It will be apparent to those of ordinary skill in the art that the invention may be embodied in various forms and that the invention. In addition, it is to be understood that while the invention has been described in conjunction with the preferred specific embodiments thereof, that the foregoing description is intended to illustrate and not limit the scope of the invention. For example, while the above description focuses on cleanliness quantification for bonding or for chemical reaction applications, the invention may be used to carry out cleanliness quantification for additional applications unrelated to biohazard detection as well, e.g., to quantify the cleanliness of lens. The cleanliness of such lenses may be quantified, for example, to determine whether they are suitable for specific transmissive or reflective applications. In such a case, the standard may be related, e.g., to optical clarity.

Aspects of different embodiments of the invention may be included or excluded from other embodiment. Other aspects, advantages and modifications within the scope of the invention will be apparent to those skilled in the art to which the invention pertains.

All patent applications and patents mentioned herein are hereby incorporated by reference in their entireties to an extent not inconsistent with the above.

What is claimed is:

1. A method for quantifying a surface's cleanliness relative to at least one contaminant, comprising:
   (a) generating interrogating radiation to which the at least one contaminant of the surface is responsive;
   (b) directing the interrogating radiation toward an article, the nonmetallic article having the surface or a surface cleaner that may hold the at least one contaminant from the surface;
   (c) detecting radiation from the article produced in a fluorescent and/or phosphorescent manner in response to the interrogating radiation by the at least one contaminant;
   (d) generating a signal that corresponds to the detected radiation; and
   (e) quantifying the surface's cleanliness by comparing the signal from the detector relative to an electronic standard unrelated to biohazard detection that corresponds to the surface in an acceptably clean state.

2. The method of claim 1, wherein step (e) comprises calculating a contaminant concentration per surface area.

3. The method of claim 1, wherein step (e) comprises calculating a particulate count.

4. The method of claim 1, further comprising, if step (e) reveals that the surface is acceptably clean, (f) placing the surface is placed in a contaminant sensitive environment.

5. The method of claim 4, wherein the contaminant sensitive environment is an oxygen facility.

6. The method of claim 4, wherein the contaminant sensitive environment allows the surface to be placed in contact with a halogen.

7. The method of claim 6, wherein the halogen is fluorine.

8. The method of claim 1, further comprising, if step (e) reveals that the surface is acceptably clean, (f) bonding the surface to another surface.

9. The method of claim 8, wherein at least one surface to be bonded comprises epoxy.

10. The method of claim 1, wherein the article comprises a lens.

11. The method of claim 1, wherein the article produce fluorescent and/or phosphorescent radiation in response to the interrogating radiation.

12. A method for quantifying a surface's bondability relative to at least one bondability parameter, comprising:
    (a) generating interrogating radiation to which the at least one bondability parameter is responsive;
    (b) directing the interrogating radiation toward a nonmetallic article having the surface or comprising a surface cleaner that may exhibit the bonability parameter;
    (c) detecting radiation from article produced in response to the interrogating radiation the at least one bondability parameter;
    (d) generating a signal that corresponds to the detected radiation; and
    (e) comparing the signal from the detector relative to a standard that corresponds to the surface in an acceptably bondable state so as to quantify the surface's bondability relative to the bondability parameter.

13. The method of claim 12, wherein the at least one bondability parameter is the surface's roughness.

14. The method of claim 12, wherein the at least one bondability parameter comprises the surface's roughness and cleanliness.

15. The method of claim 12, wherein the at least one bondability parameter comprises a measure of particulate matter.

16. The method of claim 15, wherein step (e) comprises calculating a contaminant concentration per surface area.

17. The method of claim 15, wherein step (e) comprises calculating a particulate count.

18. The method of claim 12, wherein the at least one bondability parameter comprises a measure of organic matter.

19. The method of claim 18, wherein the at least one bondability parameter comprises a measure of the organic matter comprising a hydrocarbon.

20. A method for bonding a plurality of surfaces that may or may not be contaminated by at least one surface contaminant, comprising:
    (a) generating interrogating radiation to which the at least one surface contaminant is responsive;
    (b) directing the interrogating radiation toward the at least one surface or a surface cleaner may hold any of the at least one contaminant from at least one surface;
    (c) detecting radiation from the at least one surface or the surface cleaner produced in response to the interrogating radiation by the at least one contaminant
    (d) generating a signal that corresponds to the detected radiation;
    (e) comparing the signal from the detector relative to a standard to quantify the at least one surfaces' cleanliness; and (f) applying an adhesive between the surfaces so as to bond the surfaces.

* * * * *